United States Patent
Jonsmann (10) Patent No.: US 8,865,454 B2
(45) Date of Patent: Oct. 21, 2014

(54) FLOW THROUGH SYSTEM, FLOW THROUGH DEVICE AND A METHOD OF PERFORMING A TEST

(75) Inventor: Jacques Jonsmann, Gøløse (DK)

(73) Assignee: Scandinavian Micro Biodevices APS, Farum (DK)

( * ) Notice: Subject to any disclaimer, the term of this patent is extended or adjusted under 35 U.S.C. 154(b) by 873 days.

(21) Appl. No.: 12/532,282

(22) PCT Filed: Mar. 17, 2008

(86) PCT No.: PCT/DK2008/050066
§ 371 (c)(1),
(2), (4) Date: Sep. 21, 2009

(87) PCT Pub. No.: WO2008/113361
PCT Pub. Date: Sep. 25, 2008

(65) Prior Publication Data
US 2010/0099097 A1    Apr. 22, 2010

(30) Foreign Application Priority Data
Mar. 22, 2007   (DK) ................................. 2007 00443

(51) Int. Cl.
*C12M 1/00* (2006.01)
*C12M 1/34* (2006.01)
(Continued)

(52) U.S. Cl.
CPC ....... *G01N 33/558* (2013.01); *B01L 2300/0877* (2013.01); *G01N 33/54366* (2013.01);
(Continued)

(58) Field of Classification Search
USPC .................. 435/6.1, 7.1, 283.1, 287.7, 287.9; 422/420; 436/169
See application file for complete search history.

(56) References Cited

U.S. PATENT DOCUMENTS 5,145,784 A   9/1992  Cox et al.
5,569,608 A   10/1996 Sommer
(Continued)

FOREIGN PATENT DOCUMENTS

JP   2003-294744    10/2003
WO   WO 99/64840    12/1999
(Continued)

OTHER PUBLICATIONS

International Search Report (Form PCT/ISA/210) issued in corresponding International Application No. PCT/DK2008/050066 dated Jul. 24, 2008.

*Primary Examiner* — Narayan Bhat
(74) *Attorney, Agent, or Firm* — Buchanan Ingersoll & Rooney PC (57) ABSTRACT

The invention relates to a flow through system for quantifying a target component in a liquid. The flow through system comprises a flow-through device comprising a flow path comprising a marker section, a capture section downstream to said marker section, and at least two quantification sections. The marker section comprises a non-immobilized marker. The capture section comprises a capture zone with an immobilized capture agent, and the at least two quantification sections comprise a pre-capture quantification section placed downstream to the marker section and up stream to the capture section, and a post-capture quantification section placed downstream to the capture section. The system further comprises a quantification unit for each of said quantification sections. The quantification unit(s) being arranged to quantify marker containing components and/or particles passing through said respective quantification sections. The invention also relates to a flow through device for such flow through system and a method of determining the amount of target component in a liquid using a flow through system.

39 Claims, 2 Drawing Sheets

(51) Int. Cl.

| | | |
|---|---|---|
| *C12Q 1/68* | (2006.01) | |
| *G01N 33/53* | (2006.01) | |
| *G01N 21/75* | (2006.01) | |
| *G01N 21/77* | (2006.01) | |
| *G01N 33/543* | (2006.01) | |
| *G01N 33/558* | (2006.01) | |
| *B01L 3/00* | (2006.01) | |

(52) U.S. Cl.
CPC . *B01L 2400/0406* (2013.01); *B01L 2300/0636* (2013.01); *B01L 3/5027* (2013.01)
USPC ....... 435/283.1; 435/6.1; 435/7.1; 435/287.7; 435/287.9; 422/420; 436/169

(56) References Cited

U.S. PATENT DOCUMENTS

| | | | |
|---|---|---|---|
| 5,895,750 | A | 4/1999 | Mushahwar et al. |
| 6,790,611 | B2 | 9/2004 | Lassen et al. |
| 7,192,784 | B2 * | 3/2007 | Nadaoka et al. .............. 436/518 |
| 7,247,500 | B2 * | 7/2007 | Wei et al. ...................... 436/518 |
| 2002/0132370 | A1 | 9/2002 | Lassen et al. |
| 2002/0150930 | A1 | 10/2002 | Nadaoka et al. |
| 2003/0003514 | A1 | 1/2003 | Kovalenko |
| 2003/0129665 | A1 | 7/2003 | Selvan et al. |
| 2003/0178641 | A1 | 9/2003 | Blair et al. |
| 2004/0011975 | A1 | 1/2004 | Nicoli et al. |
| 2004/0016190 | A1 | 1/2004 | Radke et al. |
| 2005/0020666 | A1 | 1/2005 | Mukherjee et al. |
| 2005/0037511 | A1 | 2/2005 | Sharrock |
| 2005/0136500 | A1 | 6/2005 | Yang et al. |
| 2006/0075965 | A1 | 4/2006 | Lee et al. |
| 2006/0240568 | A1 * | 10/2006 | Petruno et al. ................. 436/514 |
| 2007/0134810 | A1 * | 6/2007 | Yang et al. .................... 436/514 |

FOREIGN PATENT DOCUMENTS

| | | |
|---|---|---|
| WO | WO 00/20866 | 4/2000 |
| WO | WO 03/036290 | 5/2003 |
| WO | WO 2004/025301 | 3/2004 |
| WO | WO 2004/042403 | 5/2004 |
| WO | WO 2004/051277 | 6/2004 |
| WO | WO 2005/072872 | 8/2005 |
| WO | WO 2005/117556 | 12/2005 |
| WO | WO 2006/074665 | 7/2006 |
| WO | WO 2006/098752 | 9/2006 |

* cited by examiner

Fig. 3

FLOW THROUGH SYSTEM, FLOW THROUGH DEVICE AND A METHOD OF PERFORMING A TEST

TECHNICAL FIELD

The invention relates to a flow through system for use in test of a liquid such as a test for the presence of a component in a liquid.

BACKGROUND ART

Flow through devices are widely used for performing tests of different types. The tests are generally performed on liquid samples which are applied to channels of for example microfluidic size. The liquid sample is subjected to marker and is flowed over an immobilized capture probe capable of capturing marked target components.

Flow through devices are also referred to as lateral flow devices. Lateral flow devices have generally been used as quantitative assay method which can measure one or more analyte species at the same time, with a relative high sensitivity. Generally prior art lateral flow assay has a structure comprising a sample pad, to which a sample is applied, a releasing pad coated with a detector antibody, a developing membrane (typically nitrocellulose) or strip, in which components of the sample move at different rates to be individually separated and to undergo antibody-antigen reaction, and an absorption pad which is provided at the far end of the sample pad to cause the sample to keep moving. The detector antibody is fixed onto, for example, colloidal gold particles to enable the detection. Latex beads or carbon particles may be used instead of gold particles. The diagnostic kit for the lateral flow assay is generally designed to detect an analyte in a sandwich configuration comprising the analyte, the detector antibody, and a capture antibody. Upon applying a liquid sample to the sample pad of the kit, an analyte contained in the sample begins to move from a sample pad. Firstly, the analyte reacts with a detector antibody releasable adhered to a releasing pad to form an antigen-antibody conjugate, which continues to develop in this conjugated form. Then, while moving through the developing membrane, the antigen-antibody conjugate reacts once more with a capture antibody fixed on a developing membrane to form a capture antibody-antigen-detector antibody conjugate in a sandwich form. Since the capture antibody is fixed on the developing membrane, conjugates are accumulated in the area where the capture antibodies are fixed. Proteins are invisible to the naked eye. Therefore, the presence and amount of conjugates are determined by means of an amount of gold particles attached to a certain area of the developing membrane.

The lateral flow assay has been widely and conveniently used in various fields such as pregnancy diagnosis, cancer diagnosis, and microbe detection. However, since quantification cannot be performed with the naked eye and hence an exact amount of an analyte cannot be determined, its application is restricted.

US patent application 2002/0132370 describes a lateral flow quantitative assay method which can measure one or more analyte species at the same time, with high sensitivity. The method comprises the step of binding the target analyte to a capture site and a marker, while simultaneously binding a marked reference compound to a reference site adjacent to the capture site and by use of a laser-induced surface fluorescence detector directed to the capture site quantifying a plurality of analytes.

A method of reading the flow of a liquid in an assay performed using a liquid transport carrier using a photo detector is described in US 2005/0037511.

WO 2004/042403 describes a device and an instrument for the detection of an analyte in a sample, the method for detection of an analyte in a sample comprises the following steps of a) providing at least one particle structure detectable by light scattering and coated with binding entities for said analyte; b) contacting the at least one particle structure with the sample, c) illuminating the at least one particle structure and measuring the scattered light emitted by individual particle structures at least twice and d) determining a change in the spectral signature of the scattered light as a measure of the presence and/or quantity of the analyte in the sample. US 2005/0136500 describes a flow-through assay device capable of detecting the presence or quantity of an analyte of interest. The device contains a substrate printed with a channel to facilitate the flow of a test sample to a detection working electrode. The detection working electrode communicates with affinity reagents, such as redox mediators and capture ligands. For instance, capture ligands that are specific binding members for the analyte of interest are applied to the detection electrode to serve as the primary location for detection of the analyte.

A similar device which comprises an electrochemical biosensor that utilizes detection and calibration working electrodes that communicate with affinity reagents, such as redox mediators and capture ligands is described in US 2004/016190

DESCRIPTION OF INVENTION

The object of the present invention is to provide a novel flow through system and device by use of which a qualitative as well as a quantitative detection of a target compound in a liquid can be obtained in a relatively simple and economically feasible way.

This object has been achieved by the invention as it is defined in the claims.

As it will be clear from the following description, embodiments of the invention achieve other objectives and have other desired and beneficial effects.

The flow through system for quantifying a target component in a liquid according to the invention comprises a flow-through device and at least two quantification units, which may or may not be an integrated part of the flow-through device.

The flow-through device comprises an inlet for the liquid sample to be tested which inlet is placed up stream to the marker section.

The flow-through device comprises a flow path comprising a marker section, a capture section downstream to said marker section, and at least two quantification sections. The marker section comprises a non-immobilized marker, the capture section comprises a capture zone with an immobilized capture agent, and said at least two quantification sections comprise a pre-capture quantification section placed downstream to the marker section and up stream to the capture section, and a post-capture quantification section placed downstream to the capture zone, The marker section is a section of the flow path comprising said non-immobilized marker prior to the application of the liquid. The marker section extends in a length of said flow path, which length is designated the marker section length.

The capture section is a section of the flow path comprising capture zone with said immobilized capture agent. The capture section extends in a length of said flow path, which length is designated the capture section length.

The term capture zone may correspond to the 'capture site' of the prior art systems.

The immobilized capture agent is an agent which is immobilized to the capture zone, meaning that the capture agent will remain fixed to the capture zone under the condition which the flow-through device is subjected to during the performance of the flow through test.

The pre-capture quantification section placed downstream to the marker section may be placed immediately adjacent to the marker section or other sections, such as a mixing section and/or a delaying section, may be placed in between the pre-capture quantification section and the marker section.

Similarly the pre-capture quantification section placed up stream to the capture section may be placed adjacent to the capture section or other sections, such as a mixing section and/or a delaying section, may be placed in between the pre-capture quantification section and the capture section.

The post-capture quantification section placed downstream to the capture section may be placed adjacent to the capture section or other sections, such as a mixing section and/or a delaying section, may be placed in between the post-capture quantification section and the capture section.

The flow through system comprises a quantification unit for each of the quantification sections. The quantification units are arranged to quantify marker containing components and/or particles passing through said respective quantification sections.

The quantification unit may either be arranged at least partly in the flow path in the respective quantification sections for quantifying the marker flowing through said quantification sections or the quantification section may comprise a quantification window through which the quantification unit may perform the quantification.

In one embodiment at least one quantification section comprises an optically transparent quantification window, preferably each quantification section comprising an optically transparent quantification window.

By the term optically transparent is meant that the window is transparent for electromagnetic waves of at least one wavelength, preferably the optically transparent window is transparent for the wavelength used by the quantification unit for performing the quantification.

The non-immobilized marker—also referred to as the marker—may in principle be any kind of optically detectable marker. The marker may preferably be selected from the group consisting of marker particles, detectable particles colour markers, fluorescence markers, enzymes, metal particles and magnetic particles.

Such markers are well known in the art and many variations thereof are commercially available. In one embodiment the marker is a labelled conjugate, preferably a fluorescently labelled conjugate such as a flourochrome-conjugated anti-immunoglobulin.

In one embodiment the marker is a fluorescently labelled marker, the fluorescent label preferably being selected from the group consisting of fluorescent particles, quantum dots, lanthanide chelates, such as samarium (Sm), Europium (Eu) and Terbium (Tb), and fluors, such as FITC, Rhodamine green, thiadicarbocyanine, Cy2, Cy3, Cy5, Cy5.5, Lucifer Yellow, fluorescein, rhodamine 6G, tetramethylrhodamine, lissamine rhodamine B, Alexa 350, Alexa 430, Alexa 488, Alexa 532, Alexa 546, Alexa 568, Alexa 594 and Alexa 647 (the numbers in the Alexa names indicate the approximate excitation wavelength maximum in nm).

In one embodiment the marker is a labelled component preferably selected from the group consisting of antibodies, antigens, enzymes, nucleic acids, such double stranded, partly single stranded and single stranded DNA, RNA, LNA and PNA.

The marker should at least to a certain degree be capable of binding to the desired target component.

The marker may be specific to the target component or it may be non-specific to the target component. In principle all the markers will flow through the pre-capture quantification section, the markers that have been bonded to the target will be captured at the capture zone and the remaining markers will flow through the post-capture quantification section, whereby the specifically bonded target component can be calculated. However, in practice some other components which are not the target component but which may have similarities to the target component may be captured at the capture zone. If such other components also are bonded to markers non-specifically bonded thereto some error may occur. If the marker is specific to the target component, only a very little amount of such other components will be bonded to the marker and consequently the possible error margin may be reduced.

In one preferred embodiment the marker is therefore specific to the target component.

The flow through system may comprise two or more markers e.g. selected independently from the examples mentioned above. The two or more markers may be directed to the same target component or to separate target components. The flow through system may thus be used to quantify the amount of two or more target components simultaneously.

In one embodiment the immobilized capture agent and the non immobilized marker may be capable of binding to the same target component to provide a sandwich detection.

The capture zone may be provided anywhere in the capture section, e.g. such as it is known from prior art flow through systems. In one embodiment the capture zone is arranged in a pattern on at least one wall section of the flow path of said capture section.

In one embodiment the capture zone is arranged in a pattern onto or into a porous or non-porous substrate in the capture section. The substrate may be any substrate e.g. as the substrates described below The flow path in the capture section may preferably comprise a bottom wall and an opposite top wall, where the capture zone preferably is arranged on said bottom wall in said capture section, and said top wall in said capture section preferably comprises a transparent display window above at least a part of said capture zone. Such a display window may preferably be visually transparent.

It should however be observed that a display window is not essential as the quantification of the target component can be performed without observing bonding to the capture zone. Thus in one example the capture section is free of any display windows In one embodiment the immobilized capture agent is a specific binding partner to said target component. Such specific binding partners are well known to a skilled person The immobilized capture agent may for example be selected from the group consisting of antibodies, antigens, polypeptides, enzymes, nucleic acids, such double stranded, partly single stranded and single stranded DNA, RNA, LNA and PNA. Other examples of immobilized capture agents and binding partners can for example be found in the prior art references referred to above.

In one embodiment the capture section also comprises a reference zone, said reference zone comprises an immobilized reference agent which is non-specific to said target component.

Such an immobilized reference agent may e.g. be capable of binding a reference component which is different from the target component, and which reference component optionally is marked with the marker or with a reference marker different from the marker for the target component.

The immobilized reference agent may for example be selected from the group consisting of antibodies, antigens, polypeptides, enzymes, nucleic acids, such double stranded, partly single stranded and single stranded DNA, RNA, LNA and PNA.

In order to provide a highly reliable quantification in the quantification sections, the flow path in said quantification sections may preferably have a relatively small cross-sectional dimension.

In one embodiment the flow path in the quantification sections is arranged to provide a capillary flow to said liquid. This capillary flow is preferably provided by having at least one inner surface part of the flow path in the quantification sections which has a sufficiently high surface tension and/or by providing the flow path in the quantification sections with at least one cross-sectional dimension which is sufficiently small. Further information about how to provide a flow path with capillary properties may e.g. be found in WO 2006/074665.

In one embodiment the flow path in said quantification sections comprises a bottom wall and an opposite top wall and a space between said bottom wall and said top wall, said top wall preferably being essentially free of solid material, more preferably the space being filled with gas prior to introducing the liquid.

The quantification sections may preferably be in the form of flow channel sections. More preferably such quantification flow channel section is free of any solid materials, such as films and porous substrates.

In one embodiment the flow path in each of the quantification sections has at least one cross sectional dimension which is less than 1000 μm, such as less than 250 μm, such as less than 150 μm, such as less than 50 μm, such as less than 25 μm, preferably in the range of 1-100 μm.

The cross sectional dimension is measured perpendicular to the centreline of the flow path.

In one embodiment the flow path in each of said quantification sections has at least one cross sectional dimension which is smaller than the corresponding cross sectional dimension in at least one, preferably both of said marker section and said capture section.

The cross sectional dimensions of the flow path in the marker section and the capture section respectively, which corresponds to a cross-sectional dimension of the flow path in a quantification section are the cross-sectional dimensions of the flow path in the sections in question measured in parallel directions and perpendicular to the flow path centreline.

In one embodiment at least one quantification section comprises an optically transparent quantification window. The cross sectional dimension referred to above may preferably be measured perpendicular to the quantification window or at least a part of the quantification window.

In one embodiment the quantification window in each of said quantification sections has a size sufficiently large for performing a quantification of the amount of marker and/or particles in a liquid in said quantification section. The size of the quantification window may preferably be at least 0.001 $mm^2$, such as at least 0.01 $mm^2$, such as up to 2 $mm^2$, such as from 0.1 to 0.5 $mm^2$.

The quantification window may have any shape, but for most quantification units it is desired that the quantification window in each of said quantification sections has an essentially rectangular shape.

As the cross sectional area of the quantification sections preferably is less than the cross sectional area of the marker and the capture section, the volume of the quantification section may preferably also be less.

In one embodiment the capture section has a volume which is significantly larger than each of said quantification sections.

In one embodiment the capture section has a cross sectional area which is significantly larger than the cross sectional area of each of said quantification sections, the cross sectional area of the capture section preferably being at least 0.1 $mm^2$, such as at least 0.2 $mm^2$, such as up to 100 $mm^2$, such as from 0.5 to 10 $mm^2$, such as from 1 to 3 $mm^2$ The capture section may in one embodiment be arranged to provide a capillary flow to said liquid. Information about how to provide a capillary flow is provided above.

In one embodiment the flow through system and the capture section are arranged such that a flow can be provided by external applied forces.

In one embodiment the capture section comprises a substrate, such as a porous or non-porous substrate, said substrate preferably being made from one or more of the materials selected from the group consisting of polymers, metals, rubbers, fibrous material, such as glass fibers melt blown, spun bonded synthetic fibers (e.g., nylon, polyester, polyethylene, polypropylene, or polyethersulfone), semi-synthetic fibers, regenerated fibers, and inorganic fibers and mixtures; and foamed polymer, such as EPS; preferably the porous layer being made from one or more of the materials including nitrocellulose. In this embodiment a liquid flow may be provided by chromatographic forces provided by the substrate.

The film may e.g. comprise at least one non-porous layer, said non-porous layer preferably being liquid impervious, more preferably said layer being selected from the group consisting of polymers, metals and rubbers.

In one embodiment the film comprises at least two layers, such as at least 3, layers, such as 4 layers or more.

In one embodiment the film is a filter membrane, preferably a filter membrane for biological liquids, such as saliva, urine, whole blood, plasma, amniotic fluid, cerebrospinal fluid and fractions thereof.

In one embodiment the substrate is in the form of a film, preferably extending essentially in the whole width dimension of the flow path in said capture section, the film preferably has a length in the length direction of the flow path of at least 1 mm, such as at least 5 mm, such as at least 10 mm, such as between 5 and 100 mm.

In an alternative embodiment the capture section may be essentially free of non-immobilized solid material and the space may for example be filled with gas prior to introduction of the liquid.

The capture section may in principle have any length. In practice it is desired that the capture section is not too long, as this may result in the requirement for larger liquid samples for the test. For some tests the amount of sample is not a problem and in such examples the only limitation to the size of the capture section as well as the other sections is related to the handling of the device.

In one embodiment the capture section has a length in the length direction of the flow path of at least 1 mm, such as at least 5 mm, such as at least 10 mm, such as between 5 and 100 mm.

In one embodiment the marker section has a volume which is significantly larger than each of said quantification sections.

Also the marker section may in principle have any length for the same reasons as given above for the capture section.

In one embodiment the marker section has a length in the length direction of the flow path of at least 1 mm, such as at least 5 mm, such as at least 10 mm, such as between 5 and 100 mm.

In one embodiment the marker section has a cross sectional area which is significantly larger than the cross sectional area of each of said quantification sections, the cross sectional area of the capture section preferably being at least 1 mm$^2$, such as at least 5 mm$^2$, such as up to 100 mm$^2$, such as up to 50 mm$^2$, such as from 10-25 mm$^2$.

In one embodiment the marker section is arranged to provide a capillary flow to said liquid. Information about how to provide a capillary flow is provided above.

In one embodiment the flow through system and the marker section is arranged such that a flow can be provided by externally applied forces.

In one embodiment the marker section comprises a substrate, such as porous or non-porous substrate, said substrate preferably being made from one or more of the materials selected from the group consisting of polymers, metals, rubbers, fibrous material, such as glass fibers melt blown, spun bonded synthetic fibers (e.g., nylon, polyester, polyethylene, polypropylene, or polyethersulfone), semi-synthetic fibers, regenerated fibers, and inorganic fibers and mixtures; and foamed polymer, such as EPS; preferably the porous layer being made from one or more of the materials including nitrocellulose.

In one embodiment the substrate in the marker section is in the form of a film, preferably extending essentially in the whole width dimension of the flow path in said capture section, the film preferably has a length in the length direction of the flow path of at least 1 mm, such as at least 5 mm, such as at least 10 mm, such as between 5 and 100 mm.

In one embodiment the marker is applied onto or within the substrate in the marker section.

In one embodiment both the capture section and the marker section comprise a substrate. This substrates may be equal or different from each other.

In one embodiment the marker section is essentially free of solid material other than the marker, more preferably the space being filled with gas.

In order to provide a desired distribution of the marker in a liquid sample applied in the flow-through device it is desired that there should be at least a certain distance between the marker as it is arranged in the marker section and the pre-capture quantification section.

In one embodiment the marker is arranged in the marker section in a distance from said pre-capture quantification section which distance is at least 1 mm, such as at least 5 mm, such as at least 10 mm, such as between 5 and 100 mm.

The flow through device preferably comprises an opening downstream to the capture section for allowing gas to escape. The flow through device may additionally comprise an effluent section e.g. a chamber arranged downstream to the capture section for collecting the liquid sample passing out downstream of the capture section. Such an arrangement with a collection chamber is well known to the skilled person. In order to avoid escape of liquid from the flow-through device the opening for the escape of gas may be arranged such that the wall areas surrounding such a gas escape opening are relatively hydrophobic.

In one embodiment the quantification units are wholly or partly integrated with said flow through device. The quantification units may thus be wholly or partly placed in the flow path, preferably in said quantification sections. Quantification units which can be used in the present invention can today be provided in such small units to make this integrated solution possible. However in general it is desired that the quantification units are arranged externally to the flow-through device and the flow-through device may thus be a disposal unit.

In one embodiment the quantification units are therefore external units preferably arranged in a detector instrument.

Such detector instrument may for example comprise or be connected to a computer system arranged to perform calculation based on measurements obtained by the quantification units, the computer system preferably being capable of calculating the difference between the signal obtained from the quantification unit in the post-capture quantification section and the quantification unit in the pre-capture quantification section, and preferably determining the amount or number of captured target components based on a calibrated result.

In one embodiment the detector instrument is a detector robot capable of handling one or preferably a plurality of flow through devices automatically or semi automatically.

The quantification units may be any kind of detector units which are capable of providing a quantification of the marked component passing through the quantification sections.

In one embodiment the quantification units are detector units detecting the amounts of particles and/or markers which passes through said respective quantification sections using electromagnetic waves, preferably selected from the group consisting of ultra violet light, infrared light, microwave radiation and visibly light.

In one embodiment the quantification units are optical sensors, such as fluorescence polarization detectors, fluorescence fluctuation detectors, particle counting sensors, concentration detection sensors, light absorption sensors, and light scattering sensors.

Examples of useful polarization detectors are for example disclosed in WO 99/64840. Examples of useful concentration detection sensors are for example disclosed in U.S. Pat. No. 5,569,608. Examples of particle counting sensors are for example disclosed in US 2004/0011975 and WO 2004/042402 (using scattered light).

In one embodiment the quantification units are laser induced fluorescence detectors, such as laser detectors with a light emission capable of exciting the marker and comprising a photo sensor such as a photo-multiplier tube (PMT), an avalanche photodiode (ADP) or a charge coupled device (CCD).

Examples of laser induced fluorescence detectors are for example disclosed in US 2005/020666 and WO 2006/098752

In a preferred embodiment the flow through device may further comprise a reference section arranged between the marker section and the post-capture quantification section. The flow through device may preferably further comprise a third quantification section, referred to as the pre-reference quantification section, which is arranged between the marker section and the reference section.

The pre-reference quantification section may be placed immediately adjacent to one or both of the marker section and the reference section and/or one or more other sections, such as a mixing section and/or a delaying section, may be placed in between The reference section may preferably be as the capture section described above except that it does not comprise any capture zone with immobilized capture agent, the reference section may preferably be essentially identical to the capture section except for the capture zone with immobilized capture agent.

By such reference section the quantification result obtained may be even more accurate, since non-specific bonding of various components may be accounted for.

In one embodiment the pre-reference quantification section is essentially identical to the pre-capture quantification section and the post-capture quantification section.

The system may preferably further comprise a quantification unit arranged to quantify marker containing components passing through said pre-reference quantification section.

Generally it is desired that the quantification units used in a flow through system are essentially identical to each other.

According to the invention the quantification units may preferably be connected to or integrated with a detector instrument, which detector instrument comprises or is connected to a computer system arranged to perform calculation based on measurements obtained by the quantification units. The computer system may preferably be capable of calculating the difference between the signal obtained from the quantification unit in the post-capture quantification section and the quantification unit in the pre-capture quantification section, and compensating for non-specific binding by subtracting the result obtained by calculating the difference between the signal obtained from the quantification unit in the pre-capture quantification section and the quantification unit in the pre-reference quantification section, and preferably determining the amount or number of specifically captured target components based on a calibrated result.

The invention also relates to a flow through device for use in the flow through system as described above. The flow-through device may preferably have one or more of the features described above.

The invention further relates to a method of determining the amount of target component in a liquid using a flow through system as described above, the method comprises
providing a flow-through device,
providing a sample of the liquid to be tested,
applying the liquid sample in an inlet to said flow path upstream to said marker section,
allowing said liquid sample to flow downstream to and preferably beyond the capture zone,
measuring a signal by each of the quantification units, and
based on the measured signals determining the amount or number of specifically captured target components based on a calibrated result.

The skilled person will know how to calibrate the system, e.g. by performing the test on a number of liquid samples with a known concentration of the target component., providing a curve based on this result and compare the obtained result with this curve to determine the amount or number of specifically captured target components.

In one embodiment the method comprises measuring a signal by each of the quantification units in said pre-capture quantification section and said post-capture quantification section, subtracting the signal from each other and determining the amount or number of specifically captured target components based on a calibrated result.

In one embodiment the method comprises measuring a signal $C_2$ by the quantification unit in said pre-capture quantification section and measuring a signal $C_3$ by the quantification unit in said post-capture quantification section, and determining a capture signal X using the formula $$(C_2-C_3)/C_2 = X,$$

and determining the amount or number of specifically captured target components represented by X based on a calibrated result.

In one embodiment the method comprises measuring a signal $C_1$ by the quantification unit in said pre-reference quantification section, measuring a signal $C_2$ by the quantification unit in said pre-capture quantification section and measuring a signal $C_3$ by the quantification unit in said post-capture quantification section, and determining a capture signal Y using the formula $$((C_2-C_3)/C_2)/(C_1/(C_1-C_2)) = Y,$$

and determining the amount or number of specifically captured target components represented by Y based on a calibrated result.

In one embodiment of the method of the invention the quantification units are connected to or integrated with a detector instrument, said detector instrument comprises or is connected to a computer system arranged to perform calculation based on measurements obtained by the quantification units, the computer system preferably being capable of calculating the difference between the signal obtained from the quantification unit in the post-capture quantification section and the quantification unit in the pre-capture quantification section, and compensating for non-specific binding by subtracting the result obtained by calculating the difference between the signal obtained from the quantification unit in the pre-capture quantification section and the quantification unit in the pre-reference quantification section, and preferably determining the amount or number of specifically captured target components based on a calibrated result.

In one embodiment the method of the invention is used to detect at least one blood coagulation activity e.g. analogous to the method disclosed in US 2002/0132370 but providing the determination by the method disclosed above.

BRIEF DESCRIPTION OF DRAWINGS

Examples of embodiments of the invention will be described below with reference to the drawings where.

Figure 1:
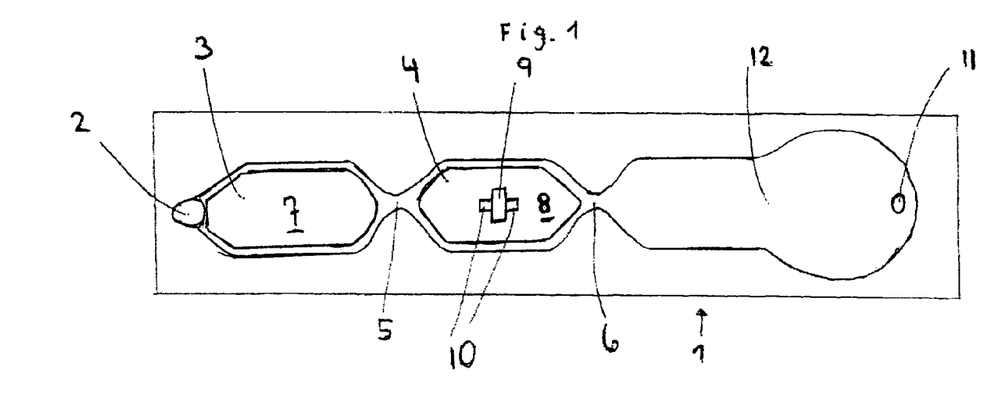
FIG. 1 is a schematic top view of a first flow-through device of the invention.

FIG. 1 shows a flow through device 1 comprising a flow path with an inlet opening 2 for a liquid sample to be tested. The flow path comprises a marker section 3, a capture section 4 downstream to said marker section, and at least two quantification sections 5, 6. The marker section comprises a substrate 7 carrying a not shown and non-immobilized marker e.g. as described above. The substrate 7 may be as described above. The capture section comprises substrate 8 and a capture zone 9 with an immobilized capture agent. The substrate 8 and the immobilized capture agent may be as described above.

The two quantification sections 5, 6 comprise a pre-capture quantification section 5 placed downstream to the marker section 3, and up stream to the capture section 4, and a post-capture quantification section 6 placed downstream to the capture section 4.

The quantification sections 5, 6 do not comprise a substrate.

The drawing is a sectional top view and the top may e.g. be covered with a not shown lid which may be totally or partly optically or even visually transparent—for example each quantification section may comprise an optically transparent quantification window, or it may be non-transparent comprising a not shown quantification unit in each of the quantification sections 5, 6.

The capture section 4 of the flow through device 1 also comprises a reference zone 10 which is capable of binding a reference component carrying a marker which may be identical to the marker for the target component of which may be a reference marker applied in the marker section 3.

The flow through device comprises an opening 11 downstream to the capture section 4 for allowing gas to escape. The flow through device additionally comprises an effluent section 12 in the form of a chamber arranged downstream to the capture section 4 for collecting the liquid sample passing out downstream of the capture section 4.

In use the liquid sample will be applied in the inlet 2. It will by use of capillary forces and/or chromatographic forces due to the substrate enter into the marker section 3 where it will be mixed with the non-immobilised marker and a possible target component which reacts with the marker. The liquid will flow further into the pre-capture quantification section 5 where it will be driven by capillary forces. At the pre-capture quantification section 5 the amount of passing marker will be quantified by a not shown quantification unit. The liquid will thereafter flow into the capture section 4 where it will be driven by use of capillary forces and/or chromatographic forces due to the substrate. In the capture section 4, marked target components will bind to the capture zone 9. Simultaneously a reference component carrying the marker or a reference marker will bind to the reference zone to indicate that the test has been terminated. The liquid will flow further into the post-capture quantification section 6 where it will be driven by capillary forces. At the post-capture quantification section 6 the amount of passing marker will be quantified by a not shown quantification unit. Finally the liquid will flow into the effluent section 12 preferably by use of capillary forces.

By use of the measurements obtained at the pre-capture quantification section 5 and the post-capture quantification section 6 the amount or number of specifically captured target components can be determined e.g. based on a calibrating curve.

Figure 2:
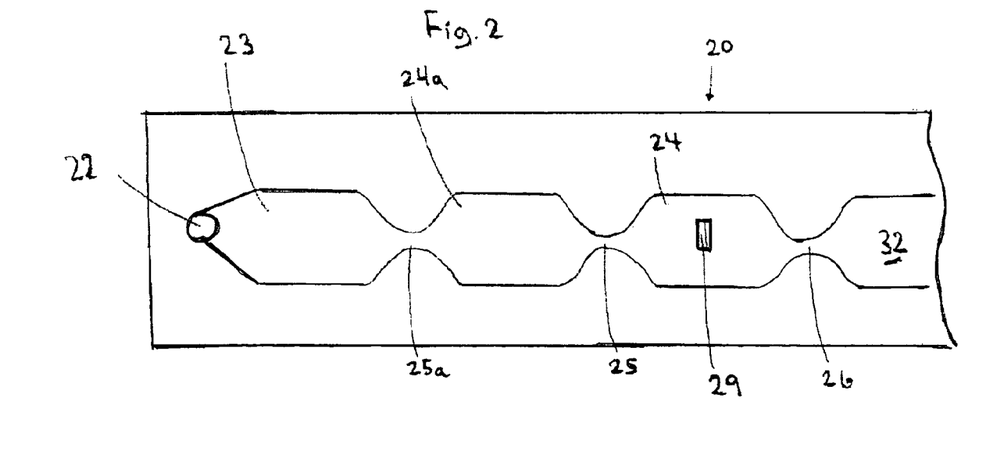
FIG. 2 is a schematic top view of a second flow-through device of the invention.

FIG. 2 shows another flow through device 20 comprising a flow path with an inlet opening 22 for a liquid sample to be tested. The flow path comprises a marker section 23, a reference section 24a downstream to said marker section and a capture section 24 downstream to said reference section, and three quantification sections 25a, 25, 26. The marker section 23 comprises a not shown and non-immobilized marker e.g. as described above. The capture section comprises a capture zone 29 with an immobilized capture agent. The reference section 24a is identical to the capture section 24 except it does not comprise a capture zone.

The quantification sections 25a, 25, 26 comprise a pre-reference quantification section 25a placed upstream to the reference section 24a, a pre-capture quantification section 25 placed downstream to the marker section 23, and a post-capture quantification section 26 placed downstream to the capture section 24.

The quantification section 25a, 25, 26 are preferably essentially identical.

The drawing is a sectional top view and the top may e.g. be covered with a not shown lid which may be totally or partly optically or even visually transparent—for example each quantification section 25a, 25, 26 may comprise an optically transparent quantification window, or it may be non-transparent comprising a not shown quantification unit in each of the quantification sections 25a, 25, 26.

The flow through device comprises an effluent section 32 with a not shown opening for the escape of gas.

In use the liquid sample will be applied in the inlet 22. It will by use of capillary forces and/or chromatographic forces due to the substrate enter into the marker section 23 where it will be mixed with the non-immobilised marker and a possible target component which reacts with the marker. The liquid will flow further into the pre-reference quantification section 25a preferably by capillary forces. At the pre-reference quantification section 25a the amount of passing marker will be quantified by a not shown quantification unit. The liquid will thereafter preferably by capillary forces flow into the reference section 24a where compounds of the liquid sample including marked compound may bind non-specifically to surfaces within the reference section 24a. The liquid will thereafter flow into the pre-capture quantification section 25 where it will be driven by capillary forces. At the pre-capture quantification section 25 the amount of passing marker will be quantified by a not shown quantification unit. The liquid will thereafter flow into the capture section 24 where it will be driven by use of capillary forces and/or chromatographic forces due to the substrate. In the capture section 24, marked target components will bind to the capture zone 29. The liquid will flow further into the post-capture quantification section 26 where it will be driven by capillary forces. At the post-capture quantification section 26 the amount of passing marker will be quantified by a not shown quantification unit. Finally the liquid will flow into the effluent section 32 preferably by use of capillary forces.

By use of the measurements obtained at the pre-reference quantification section 25a, the pre-capture quantification section 25 and the post-capture quantification section 26, the amount or number of specifically captured target components can be determined e.g. based on a calibrating curve.

Figure 3:
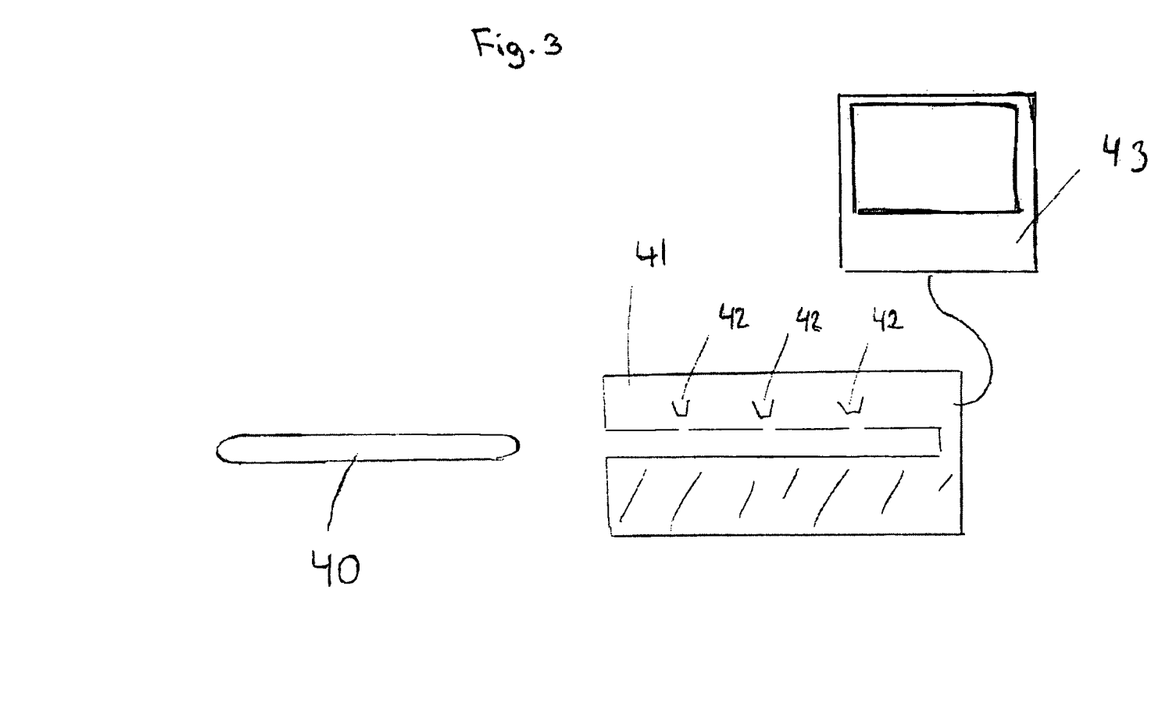
FIG. 3 is a schematic drawing of a flow through system of the invention.

FIG. 3 shows a flow through system of the invention comprising a flow-through device e.g. as the flow-through device shown in FIG. 2, and three quantification units 42 integrated with a detector instrument 41, said detector instrument 41 comprises or is connected to a computer system 43 arranged to perform calculation based on measurements obtained by the quantification units 42, the computer system 43 preferably being capable of determining the amount or number of specifically captured target components based on the measurements obtained by the quantification units 42 and calibration data.

The figures are schematic and simplified for clarity, and they merely show details which are essential to the understanding of the invention, while other details are left out.

The invention claimed is:

1. A flow through system for quantifying a target component in a liquid, said flow through system comprising a flow-through device comprising a flow path comprising a marker section, a capture section downstream to said marker section, and
at least two quantification sections,
said marker section comprises a non-immobilized marker,
said capture section comprises a capture zone with an immobilized capture agent, and
said at least two quantification sections comprise a pre-capture quantification section placed downstream to the marker section and upstream to the capture section, and a post-capture quantification section placed downstream to the capture section,
said quantification sections are in form of flow channel sections free of solid material selected from films or porous substrates, wherein said flow path in each of said quantification sections has at least one cross sectional dimension which is smaller than the corresponding cross sectional dimension in at least one, of said marker section and said capture section, said system further comprise a quantification unit for each of said quantification sections, said quantification unit for each of said quantification sections being arranged to quantify marker containing components or particles passing through said respective quantification sections.

2. The flow through system as claimed in claim 1 wherein each quantification section comprises an optically transparent quantification window.

3. The flow through system as claimed in claim 1 wherein said marker section comprises at least one non-immobilized marker selected from marker particles, detectable particles colour markers, fluorescence markers, enzymes, antibodies, antigens, nucleic acids, metal particles or magnetic particles.

4. The flow through system as claimed in claim 1 wherein said capture zone is arranged in a pattern on at least one wall section of the flow path in said capture section.

5. The flow through system as claimed in claim 1 wherein said immobilized capture agent is immobilized in said capture zone, said immobilized capture agent being a specific binding partner to said target component.

6. The flow through system as claimed in claim 1 wherein said immobilized capture agent is selected from antibodies, antigens, polypeptides, enzymes or, nucleic acids.

7. The flow through system as claimed in claim 1 wherein said capture section also comprises a reference zone, said reference zone comprises an immobilized reference agent which is non-specific to said target component.

8. The flow through system as claimed in claim 7 wherein said immobilized reference agent is capable of binding to the marker.

9. The flow through system as claimed in claim 7 wherein said immobilized reference agent is selected from antibodies, antigens, polypeptides, enzymes or nucleic acids.

10. The flow through system as claimed in claim 1 wherein said flow path in each of said quantification sections has at least one cross sectional dimension which is less than 1000 µm.

11. The flow through system as claimed in claim 10, wherein at least one quantification section comprises a transparent quantification window and wherein said cross sectional dimension is perpendicular to said quantification window or at least a part of said quantification window.

12. The flow through system as claimed in claim 1 wherein the capture section has a volume which is significantly larger than each of said quantification sections.

13. The flow through system as claimed in claim 1 wherein at least one of the capture section and the marker section comprises a substrate, selected from a porous or non-porous substrate.

14. The flow through system as claimed in claim 1 wherein at least one of the capture section and the marker section is essentially free of non-immobilized solid material.

15. The flow through system as claimed in claim 1 wherein the marker section has a volume which is significantly larger than each of said quantification sections.

16. The flow through system as claimed in claim 1 wherein the marker is arranged in said marker section in a distance from said pre-capture quantification section which distance is at least 1 mm.

17. The flow through system as claimed in claim 1 wherein the quantification units are wholly or partly placed in said quantification sections.

18. The flow through system as claimed in claim 1 wherein the quantification units are external units arranged in a detector instrument.

19. The flow through system as claimed in claim 1 wherein the quantification units are detector units detecting the amounts of particles or markers which pass through said respective quantification sections using electromagnetic waves, preferably selected from the group consisting of ultra violet light, infrared light, microwave radiation and visibly light.

20. The flow through system as claimed in claim 1 wherein the quantification units are optical sensors.

21. The flow through system as claimed in claim 1 wherein the flow through device further comprises a reference section arranged between the marker section and the post-capture quantification section, said flow through device further comprises a third quantification section (pre-reference quantification section) arranged between the marker section and said reference section.

22. The flow through system as claimed in claim 21 wherein said reference section not comprise any capture zone with immobilized capture agent, the reference section being essentially identical to the capture section except for the capture zone with immobilized capture agent.

23. The flow through system as claimed in claim 21 wherein said pre-reference quantification section is essentially identical to the pre-capture quantification section and the post-capture quantification section.

24. The flow through system as claimed in claim 21 wherein said system further comprises a quantification unit arranged to quantify marker containing components passing through said pre-reference quantification section.

25. The flow through system as claimed in claim 1 wherein said capture zone is arranged in a pattern on at least one wall section of the flow path in said capture section, the flow path in said capture section comprises a bottom wall and an opposite top wall, said capture zone being arranged on said bottom wall in said capture section, and said top wall in said capture section comprises a transparent display window above at least a part of said capture zone.

26. The flow through system as claimed in claim 1 wherein the quantification units are optical sensors selected from laser induced fluorescence detectors, fluorescence polarization detectors, fluorescence fluctuation detectors, particle counting sensors, concentration detection sensors, light absorption sensors, or light scattering sensors.

27. The flow through system as claimed in claim 1 wherein the quantification units are fluorescence polarization detectors, fluorescence fluctuation detectors, particle counting sensors, concentration detection sensors, light absorption sensors, or light scattering sensors.

28. The flow through system as claimed in claim 1, wherein the flow path in said quantification sections comprises a bottom wall and an opposite top wall and a space between said bottom wall and said top wall, wherein said space being filled with gas prior to introducing said liquid.

29. A flow through device for quantifying a target component in a liquid, said flow through device comprising
a flow path comprising a marker section,
a capture section downstream to said marker section, and at least two quantification sections,
said marker section comprises a non-immobilized marker, said capture section comprises a capture zone with an immobilized capture agent, and
said at least two quantification sections comprise a pre-capture quantification section placed downstream to the marker section and upstream to the capture zone, said quantification sections are in form of flow channel sections free of solid material selected from films or porous substrates, wherein said flow path in each of said quantification sections has at least one cross sectional dimension which is smaller than the corresponding cross sectional dimension in at least one, of said marker section and said capture section, a post-capture quantification section placed downstream to the capture zone and wherein said device further comprises a quantification unit for each of said quantification sections, said quantification unit for each of said quantification sections being arranged to quantify marker containing components or particles passing through said respective quantification sections and being wholly or partly integrated with said flow through device.

30. The flow through device as claimed in claim 29 wherein the quantification units are wholly or partly placed in said quantification sections, the quantification units are detector units arranged to detecting amounts of particles or markers which pass through said respective quantification sections using electromagnetic waves.

31. The flow through device as claimed in claim 30 wherein the flow through device further comprises a reference section arranged between the marker section and the post-capture quantification section, said flow through device further comprises a third quantification section (pre-reference quantification section) arranged between the marker section and said reference section.

32. The flow through device as claimed in claim 31 wherein said pre-reference quantification section is essentially identical to the pre-capture quantification section and the post-capture quantification section.

33. The flow through device as claimed in claim 29, wherein the flow path in said quantification sections comprises a bottom wall and an opposite top wall and a space between said bottom wall and said top wall, wherein said space being filled with gas prior to introducing said liquid.

34. A flow through system for quantifying a target component in a liquid, said flow through system comprising:
a flow-through device comprising a flow path comprising a marker section, said marker section comprises a non-immobilized marker for binding to the target component,
a capture section downstream to said marker section, said capture section comprises a capture zone with an immobilized capture agent for binding the non-immobilized marker bound to the target component,
a pre-capture quantification section placed downstream to the marker section and upstream to the capture section,
a post-capture quantification section placed downstream to the capture section,
said quantification sections are in form of flow channel sections free of solid material selected from films or porous substrates, wherein said flow path in each of said quantification sections has at least one cross sectional dimension which is smaller than the corresponding cross sectional dimension in at least one, of said marker section and said capture section,
a quantification unit for each of said quantification sections, said quantification unit for each of said quantification sections includes means for quantifying the marker containing components or particles passing through said respective quantification sections, said quantification units each generating a signal relating to a quantity of marker flowing through the respective quantification sections, and
means for comparing the signals from the quantification units for determining a value that reflects the amount of specifically captured target.

35. A method of determining the amount of target component in a liquid using a flow through system as defined in claim 1, comprising
providing a flow-through device,
providing a sample of the liquid to be tested,
applying the liquid sample in an inlet to said flow path upstream to said marker section,
allowing said liquid sample to flow downstream to and preferably beyond the capture zone,
measuring a signal by each of the quantification units, and
based on the measured signals determining the amount or number of specifically captured target components based on a calibrated result.

36. The method of determining the amount of target component in a liquid as claimed in claim 35, the method comprising measuring a signal by each of the quantification units in said pre-capture quantification section and said a post-capture quantification section, subtracting the signal from each other and determining the amount or number of specifically captured target components based on a calibrated result.

37. The method of determining the amount of target component in a liquid as claimed in claim 35, the method comprising measuring a signal $C_2$ by the quantification unit in said pre-capture quantification section and measuring a signal $C_3$ by the quantification unit in said post-capture quantification section, and determining a capture signal X using the formula $$(C_2-C_3)/C_2)=X,$$

and determining the amount or number of specifically captured target components represented by X based on a calibrated result.

38. The method of determining the amount of target component in a liquid as claimed in claim 35, the method comprising measuring a signal $C_1$ by the quantification unit in said pre-reference quantification section, measuring a signal $C_2$ by the quantification unit in said pre-capture quantification section and measuring a signal $C_3$ by the quantification unit in said post-capture quantification section, and determining a capture signal Y using the formula $$((C_2-C_3)/C_2)/(C_1/(C_1-C_2))=Y,$$

and determining the amount or number of specifically captured target components represented by Y based on a calibrated result.

39. The method of determining the amount of target component in a liquid as claimed in claim 35, wherein the quantification units are connected to or integrated with a detector instrument, said detector instrument comprises or is connected to a computer system arranged to perform calculation based on measurements obtained by the quantification units, the computer system being capable of calculating the difference between the signal obtained from the quantification unit in the post-capture quantification section and the quantification unit in the pre-capture quantification section, and compensating for non-specific binding by subtracting the result obtained by calculating the difference between the signal obtained from the quantification unit in the pre-capture quantification section and the quantification unit in the pre-reference quantification section, and determining the amount or number of specifically captured target components based on a calibrated result.

* * * * *